United States Patent [19]

Franke et al.

[11] Patent Number: 4,740,597
[45] Date of Patent: Apr. 26, 1988

[54] PROCESS FOR THE CONTINUOUS REACTION OF CYANURIC FLUORIDE WITH SULFO-CONTAINING AROMATIC AMINES

[75] Inventors: Karlheinz Franke, Basel, Switzerland; Edmond Ruhlmann, Saint-Louis, France

[73] Assignee: Ciba-Geigy Corporation, Ardsley, N.Y.

[21] Appl. No.: 767,940

[22] Filed: Aug. 21, 1985

[30] Foreign Application Priority Data

Aug. 21, 1984 [CH] Switzerland .................. 3992/84

[51] Int. Cl.$^4$ .................. C07D 251/44; C07D 251/50; C07D 251/70
[52] U.S. Cl. .................................. 544/211; 544/196; 544/197; 544/204; 544/208; 544/194; 544/189; 544/181; 534/637; 534/618; 534/638
[58] Field of Search ................ 544/211, 187, 194, 189

[56] References Cited

U.S. PATENT DOCUMENTS

| | | | |
|---|---|---|---|
| 4,189,570 | 2/1980 | Bonometti et al. | 544/211 |
| 4,189,576 | 2/1980 | Altorfer et al. | 544/211 |
| 4,255,325 | 3/1981 | Harms | 544/187 |
| 4,485,041 | 11/1984 | Hoyer et al. | 544/187 |
| 4,503,224 | 3/1985 | Harms | 544/187 |

FOREIGN PATENT DOCUMENTS

| | | |
|---|---|---|
| 2903594 | 8/1980 | Fed. Rep. of Germany . |
| 872313 | 7/1961 | United Kingdom . |
| 1569246 | 6/1980 | United Kingdom . |

OTHER PUBLICATIONS

Chemical Abstracts, vol. 94, (1981), 94:4942 x, (Wunderlich et al.).

Primary Examiner—John M. Ford
Attorney, Agent, or Firm—Kevin T. Mansfield; Edward McC. Roberts

[57] ABSTRACT

The reaction of cyanuric fluoride with amines to form monocondensation products is possible in high yields by subjecting the educts to rapid thorough mixing and then bringing the reaction to completion under plug flow conditions.

15 Claims, No Drawings

PROCESS FOR THE CONTINUOUS REACTION OF CYANURIC FLUORIDE WITH SULFO-CONTAINING AROMATIC AMINES

The present invention relates to a process for the continuation reaction of cyanuric fluoride with amines, which comprises passing cyanuric fluoride and an aqueous solution of the amine simultaneously and continuously into a first reactor, effecting thorough mixing there, then passing the reaction mixture into a second reactor in which only little backmixing but good radial mixing occurs, and completing the reaction there.

German Offenlegungsschrift No. 2,746,109 already discloses a process for the continuous reaction of cyanuric fluoride with aminobenzenesulfonic acids or aminonaphthalenesulfonic acids. According to the indications of this German Offenlegungsschrift, the reactor used is a continuous throughflow "ideal kettle" with complete backmixing of the reaction material in the reactor. However, the operating method described there is only of limited applicability to the reaction of cyanuric fluoride with aminonaphtholsulfonic acids, since considerable amounts of byproducts are obtained in this case.

The present invention has for its object to find a process which permits the continuous reaction of cyanuric fluoride with aminonaphtholsulfonic acids to give monocondensation products, i.e. compounds in which 1 mol of cyanuric fluoride reacts with 1 mol of aminonaphtholsulfonic acid, in improved yield and/or purity.

This object is achieved with the process according to the invention by first mixing the reactants in a first reactor and then completing the reaction in a second reactor in which there is only little backmixing but good radial mixing. Surprisingly, this operating method also produces the reaction products of 1 mol of aminonaphtholsulfonic acid with 1 mol of cyanuric fluoride in high yield and purity, and the process according to the invention is also more suitable in many cases than the known process as regards the reaction of aminobenzenesulfonic or aminonaphthalenesulfonic acids with cyanuric fluoride.

The process according to the invention can be carried out with ammonia or aliphatic amines, for example ethanolamine or taurine. However, preference is given to the use of sulfo-containing aromatic amines.

Suitable sulfo-containing aromatic amines are for example: 1-aminobenzene-2-sulfonic acid, 1-aminobenzene-3-sulfonic acid, 1-aminobenzene-4-sulfonic acid, 1-amino-4-methylbenzene-3-sulfonic acid, 1-amino-4-methoxybenzene-3-sulfonic acid, 1-amino-2-methylbenzene-4-sulfonic acid, 1-amino-3-methylbenzene-4-sulfonic acid, 1-aminobenzene-3,5-disulfonic acid, 2-amino-5-sulfobenzoic acid, 1-aminonaphthalene-4-sulfonic acid, 1-aminonaphthalene-5-sulfonic acid, 1-aminonaphthalene-6-sulfonic acid, 2-aminonaphthalene-5-sulfonic acid, 2-aminonaphthalene-7-sulfonic acid, 2-aminonaphthalene-4,8-disulfonic acid, 2-aminonaphthalene-5,7-disulfonic acid, 1,4-diaminobenzene-2,5-disulfonic acid, 1,3-diaminobenzene-4-sulfonic acid, 1,4-diaminobenzene-2-sulfonic acid, 1,3-diaminobenzene-4,6-disulfonic acid, 1-amino-5-hydroxynaphthalene-7-sulfonic acid, 1-amino-8-hydroxynaphthalene-4-sulfonic acid, 1-amino-8-hydroxynaphthalene-3-sulfonic acid, 1-amino-8-hydroxynaphthalene-5-sulfonic acid, 2-amino-5-hydroxynaphthalene-7-sulfonic acid, 2-amino-6-hydroxynaphthalene-8-sulfonic acid, 2-amino-8-hydroxynaphthalene-6-sulfonic acid, 2-methylamino-8-hydroxynaphthalene-6-sulfonic acid, 2-methylamino-5-hydroxynaphthalene-7-sulfonic acid, 2-ethylamino-5-hydroxynaphthalene-7-sulfonic acid, 2-methylamino-8-hydroxynaphthalene-6-sulfonic acid, 2-ethylamino-8-hydroxynaphthalene-6-sulfonic acid, 1-amino-6-hydroxynaphthalene-3,8-disulfonic acid, 1-amino-8-hydroxynaphthalene-3,6-disulfonic acid, 1-amino-8-hydroxynaphthalene-2,4-disulfonic acid, 1-amino-8-hydroxynaphthalene-4,6-disulfonic acid, 1-amino-8-hydroxynaphthalene-3,5-disulfonic acid, 2-amino-5-hydroxynaphthalene-7,1-disulfonic acid and 2-amino-8-hydroxynaphthalene-3,6-disulfonic acid.

The process according to the invention is particularly suitable for the reaction of cyanuric fluoride with 2-amino-5-hydroxynaphthalene-7-sulfonic acid, 2-amino-8-hydroxynaphthalene-6-sulfonic acid, 1-amino-8-hydroxynaphthalene-4,6-disulfonic acid or especially 1-amino-8-hydroxynaphthalene-3,6-disulfonic acid or 1-aminobenzene-3-sulfonic acid.

The sulfo-containing amines are used as aqueous solutions. The cyanuric fluoride can be used in appreciable excess. It is advantageous to use cyanuric fluoride and amine in a molar ratio of 0.8:1 to 1.5:1, preferably 1:1 to 1.2:1, in particular 1:1 to 1.08:1.

The amine solution preferably has added to it a buffer substance which has the effect that during the reaction a pH between 1 and 8, preferably between 1 and 4, is maintained, depending on the buffer substance. Suitable buffer substances are for example alkali metal fluorides, in particular NaF. These buffer substances are generally used in an amount of 0.5 to 2, preferably 0.8 to 1.2, mol per mol of amine.

The educts are passed simultaneously and continuously into a first reactor where thorough mixing takes place, for example by means of a suitable disperser unit, such as a rotor-stator mixing head, using about 1000 to 25,000 revolutions per minute or an ultrasonic mixing chamber or a static mixing device. The dwell time in this first reactor should be as short as possible, but should nonetheless be long enough for sufficient mixing to take place. In general, the dwell time in the first reactor is at most 5 seconds, preferably at most 1 second.

Even during this time a partial reaction takes place between the cyanuric fluoride and the amine. It has been found to be advantageous, in particular if the amine used is an aminonaphtholsulfonic acid, if the conversion in the first reactor is at most 50%, preferably at most 30%. This conversion is obtained by the first reactor having a small volume and/or by means of a short dwell time.

From the first reactor the reaction mixture passes into a second reactor, where the reaction is brought to completion. The second reactor can in general be any reactor in which there is only little backmixing but good radial mixing. Preference is given to using a tubular reactor having a good plug flow profile and operating in the turbulent flow range. Tubular reactors having laminar flow are likewise usable provided they are equipped with suitable static mixing elements for improving radial mixing. This second reactor may be cooled in order to keep the temperature within the desired range. The dwell time of the reaction mixture in the second reactor depends, inter alia, on the nature of the amine and the temperature, and is in general between about 30 seconds and 5 minutes.

The reaction according to the invention can be carried out relatively low temperatures, at room temperature or at elevated temperatures, for example 120° C.

Preference is given to operating within the range between 0° and 50° C., in particular between 0° and 20° C.

The resulting reaction products from 1 mol of amine and 1 mol of cyanuric fluoride can be isolated, but they are preferably further processed without intermediate isolation, for example into reactive dyes by reaction with an amino-containing dye or by reaction with aromatic amine and subsequent coupling with a diazonium compound. This further processing can be carried out discontinuously or continuously in known manner.

The process according to the invention produces the condensation products from cyanuric fluoride and sulfo-containing aromatic amines in many cases in distinctly higher purity than the processes customary heretofore. This has a favourable effect on the quality of the reactive dyes prepared from the condensation products, since customarily the condensation products are further processed without intermediate purification.

The following examples serve to illustrate the invention without limiting the invention thereto. The temperatures are given in degrees Celsius.

EXAMPLE 1

4.7 ml/min of cyanuric fluoride at a temperature of about 25° C. and 300 ml/min of an aqueous solution at 0° C. containing 15.95 g of 1-amino-8-hydroxynaphthalene-3,6-disulfonic acid, 2.1 g of NaF and 5 ml of 30% NaOH are fed simultaneously and continuously via separate lines into a first reactor (dispersing unit).

In the reactor, which has a capacity of about 1 ml, a dispersing device produces high turbulence to obtain uniform, fast suspension of the disperse phase during a dwell time of 0.2–1 sec. At the same time about 20–50% conversion takes place there.

From the first reactor the reaction mixture is passed through a cooled tubular reactor which has a good plug flow profile and a capacity of 340 ml. The dwell time in the tubular reactor is about 60 sec. The reaction mixture, which leaves the reactor at a temperature of 3°, contains the compound of the formula

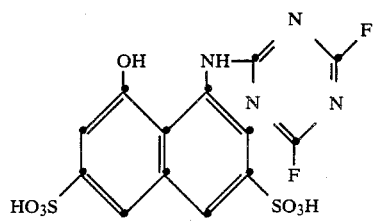

in a yield of 85%, based on starting 1-amino-8-hydroxynaphthalene-3,6-sulfonic acid.

The reaction mixture obtained is passed into a stirred kettle, where it is converted into a red reactive dye in accordance with the following method:

To the reaction mixture is added, per mol of the condensation product described above, a solution containing 1 mol of p-chloroaniline, 500 ml of water and 100 ml of 32% hydrochloric acid, and a pH of 6.0 is set with 20% NaOH in the course of 10–20 minutes.

The resulting solution is added to a diazonium salt suspension at 0°–5°, obtained by diazotisation of 1 mol of 2-naphthylamine-1,5-disulfonic acid in conventional manner. At at most 10° a pH of 7.5 is set with 30% sodium hydroxide solution and thorough stirring, and stirring is continued for a further hour at pH 7.5 and 10°.

This gives the dye of the formula

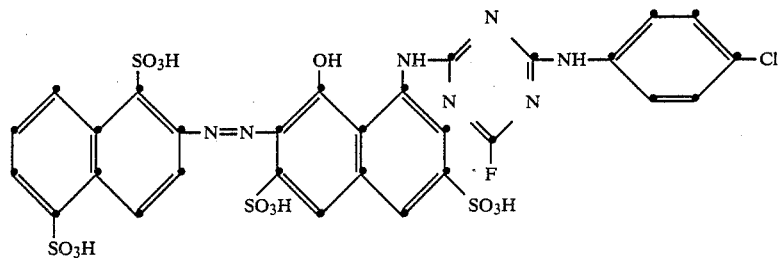

in a yield of 80–85%, based on starting 1-amino-8-hydroxynaphthalene-3,6-disulfonic acid. The dye dyes cellulose material in a very wet-fast red shade.

The processess customary heretofore, i.e. carrying out the condensation of cyanuric fluoride with 1-amino-8-hydroxynaphthalene-3,6-disulfonic acid in a stirred kettle, and otherwise using the same operating method produce the dye described above only in about 60–65% yield and, what is more, contaminated with red compounds which, inter alia, are responsible for the poor wet fastness properties of the dyeings obtainable on cellulose material.

Example 1 is repeated, except that the reaction mixture is made to leave the reactor at a temperature of 20° C. and is immediately processed further, affording the end product of the abovementioned formula in the same yield.

In the reaction mixture it is also possible to use LiOH in place of NaOH and in turn leave out NaF.

EXAMPLE 2

Example 1 is repeated, except that the first reactor is simultaneously and continuously charged via separate lines with 4.9 ml/min of cyanuric fluoride and 300 ml/min of an aqueous solution at 0° containing 11.95 g of 2-amino-5-hydroxynaphthalene-7-sulfonic acid and 25 ml of 2N lithium hydroxide, affording in good yield the compound of the formula

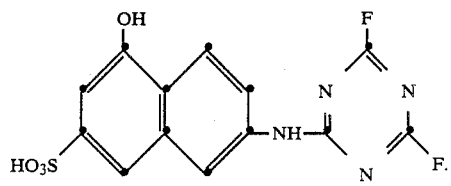

The reaction mixture obtained is passed into a stirred kettle, where it is converted into an orange reactive dye by the following method:

1 to 1.2 mol of N-ethylaniline are added per mol of the condensation product described above and a pH of 6.0 is set with 20% NaOH in the course of 10 to 30 minutes. The resulting solution is added to a diazonium salt suspension at 0° to 5°, which has been obtained by diazotisation of 1 mol of 2-naphthylamine-1,5-disulfonic acid in conventional manner. At at most 10° a pH of 7.5 is set with 30% NaOH. Salting out and filtering off gives in good quality and yield the orange reactive dye of the formula

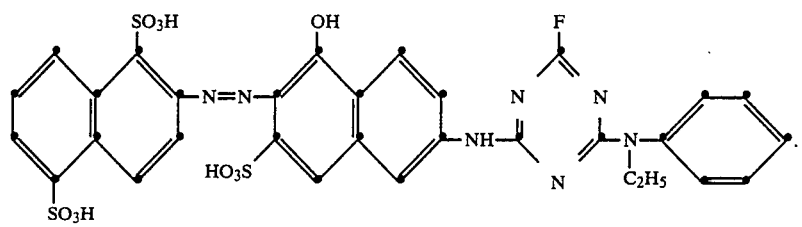

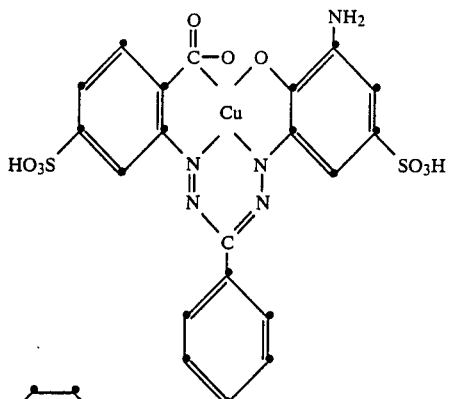

EXAMPLE 3

4.27 ml/min of cyanuric fluoride at a temperature of about 25° and 300 ml/min of an aqueous solution at 0° containing 8.65 g of metanilic acid, 2.1 g of NaF and 5 ml of 30% NaOH are fed simultaneously and continuously via separate lines into a first reactor (dispersing unit).

In the reactor, which has a capacity of about 1 ml, a dispersing device produces high turbulence to obtain uniform, fast suspension of the disperse phase during a dwell time of 0.2–1 sec. At the same time about 20–50% conversion takes place there.

From the first reactor the reaction mixture is passed through a cooled tubular reactor which has a good plug flow profile and a capacity of 340 ml. The dwell time in the tubular reactor is about 60 sec. The reaction mixture, which leaves the reactor at a temperature of 3°, contains the compound of the formula

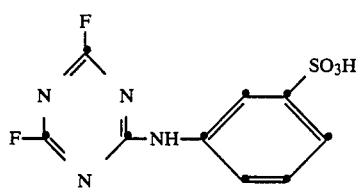

in a yield of 95–97%, based on starting metanilic acid.

The reaction mixture obtained is passed into a stirred kettle, it is treated at room temperature per mol of the condensation product described above with a solution consisting of 3000 ml of water, 0.9 mol of the formazan dye of the formula and sufficient 30% NaOH to set a pH of 7.5. The reaction mixture is stirred for 45 minutes, during which a pH of 7.5 is maintained by addition of 30% NaOH. The resulting blue dye is isolated by spray-drying.

EXAMPLE 4

Example 3 is repeated, except that a solution of 2-chloroaniline-5-sulfonic acid is used in place of metalinic acid, affording the compound of the formula

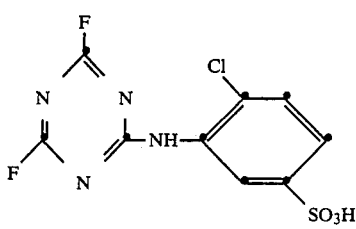

in a yield of 90 to 96%, based on starting amine.

This unstable intermediate can be readily condensed at pH 7.0 to 8.0 with one equivalent of 1,3-phenylenediamine-4-sulfonic acid to give the assymetrical condensation product

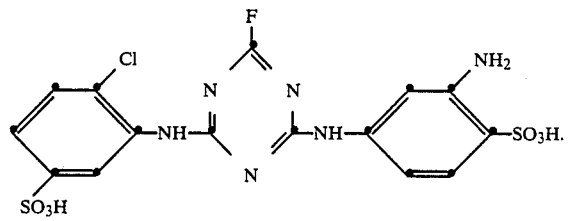

Diazotisation in conventional manner and coupling onto 1-ethyl-6-hydroxy-4-methyl-2-pyridone-3-carboxamide gives the dye of the formula

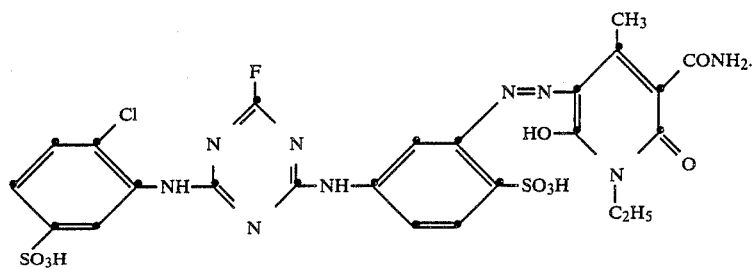

EXAMPLE 5

Example 3 or 4 is repeated, except that a solution of aniline-2,5-disulfonic acid is used and cyanuric fluoride is used in a stoichiometric ratio or in an excess of up to 15%, affording the intermediate of the formula

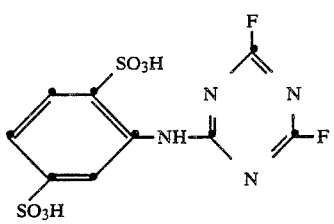

in a yield of more than 92%, based on the amine.

This useful intermediate, if reacted further at pH 7.0 with aminoazo or disazo dyes or other chromophores, produces dyes having interesting application properties, for example

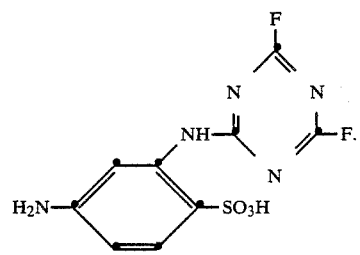

The reaction mixture obtained, if reacted with suitable amines, for example m-chloroaniline, to give the asymmetrical condensation product

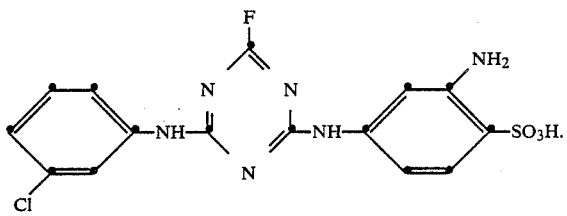

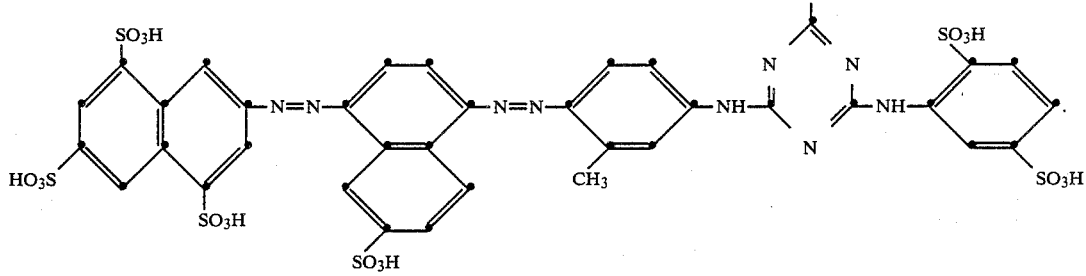

EXAMPLE 6

4.5 to 5.0 ml of cyanuric fluoride and 300 ml/min of an aqueous solution at 0° containing 9.4 g of 1,3-phenylenediamine-4-sulfonic acid, 2.1 g of NaF and 5 ml of NaOH are fed in simultaneously as described in the preceding examples, affording in high yield the compound of the formula Diazotisation of this product in conventional manner and coupling onto the known monoazo dye sulfanilic acid $\xrightarrow{acid}$ H acid, leads in a single-stage process to the known blue reactive dye of the formula

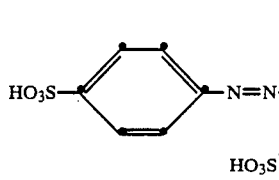 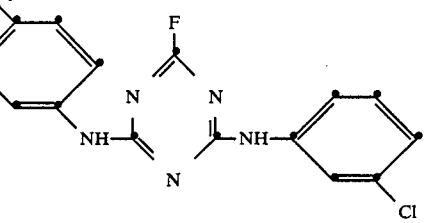

We claim:

1. A process for the continuous reaction of cyanuric fluoride with amines, which comprises passing cyanuric fluoride and an aqueous solution of an aminonaphthalenesulfonic acid simultaneously and continuously into a flow reactor, performing thorough mixing there, then passing the reaction mixture into a second reactor in which there is only little back-mixing but good radial mixing, and completing the reaction there, wherein the reaction is carried out at 0° to 50° C. and at a pH between 1 and 8, and wherein the conversion in the first reactor is at most 50%.

2. A process according to claim 1, wherein the reaction is carried out at 0° to 20° C.

3. A process according to claim 1, wherein the thorough mixing is effected within at most 5 seconds.

4. A process according to claim 3, wherein the thorough mixing is effected within at most 1 second.

5. A process according to claim 1, wherein the conversion in the first reactor is at most 30%.

6. A process according to claim 1, wherein the second reactor is a tubular reactor having a good plug flow profile.

7. A process according to claim 1, wherein cyanuric fluoride and amine are used in a molar ratio of 0.8:1 to 1.5:1.

8. A process according to claim 7, wherein cyanuric fluoride and amine are used in a molar ratio of 1:1 to 1.2:1.

9. A process according to claim 8, wherein cyanuric fluoride and amine are used in a molar ratio of 1:1 to 1.08:1.

10. A process according to claim 1, wherein the amine used is an aminonaphthalenesulfonic acid.

11. A process according to claim 1, wherein the amine used is 2-amino-5-hydroxynaphthalene-7-sulfonic acid, 2-amino-8-hydroxynaphthalene-6-sulfonic acid, 1-amino-8-hydroxynaphthalene-4,6-disulfonic acid, or 1-amino-8-hydroxynaphthalene-3,6-disulfonic acid.

12. A process according to claim 1, wherein the reaction is carried out in the presence of a buffer at a pH between 1 and 4.

13. A process according to claim 12, wherein the buffer used is an alkali metal fluoride, preferably NaF.

14. A process according to claim 12 or 13, wherein the buffer is used in an amount of 0.5 to 2, mol per mol of amine.

15. A process according to claim 14, wherein the buffer is used in an amount of 0.8 to 1.2 mol per mol of amine.

* * * * *